United States Patent
Bell

(10) Patent No.: US 9,678,956 B2
(45) Date of Patent: Jun. 13, 2017

(54) DATA CAPTURING AND STRUCTURING METHOD AND SYSTEM

(75) Inventor: Therasa Bell, Boise, ID (US)

(73) Assignee: KNO2 LLC, Boise, ID (US)

(*) Notice: Subject to any disclaimer, the term of this patent is extended or adjusted under 35 U.S.C. 154(b) by 0 days.

(21) Appl. No.: 13/399,581

(22) Filed: Feb. 17, 2012

(65) Prior Publication Data

US 2013/0218917 A1  Aug. 22, 2013

(51) Int. Cl.
*G06F 17/30* (2006.01)
*G06F 19/00* (2011.01)

(52) U.S. Cl.
CPC ...... *G06F 17/30011* (2013.01); *G06F 19/322* (2013.01)

(58) Field of Classification Search
None
See application file for complete search history.

(56) References Cited

U.S. PATENT DOCUMENTS

| | | | |
|---|---|---|---|
| 8,073,712 B2 | 12/2011 | Jacobus et al. | |
| 2006/0173708 A1* | 8/2006 | Vining et al. | 705/2 |
| 2007/0192133 A1 | 8/2007 | Morgan | |
| 2007/0192143 A1* | 8/2007 | Krishnan et al. | 705/3 |
| 2008/0177537 A1* | 7/2008 | Ash | G06F 19/322 704/235 |
| 2008/0228716 A1* | 9/2008 | Dettinger | G06F 17/30923 |
| 2008/0306773 A1 | 12/2008 | Rosenfeld et al. | |
| 2009/0138283 A1* | 5/2009 | Brown | 705/3 |
| 2009/0232398 A1* | 9/2009 | Martin et al. | 382/187 |
| 2010/0036834 A1* | 2/2010 | Bandas | 707/5 |
| 2011/0010401 A1* | 1/2011 | Adams et al. | 707/805 |
| 2011/0225000 A1* | 9/2011 | Selim | 705/2 |
| 2011/0225176 A1* | 9/2011 | Siegel et al. | 707/756 |
| 2012/0035959 A1* | 2/2012 | Berdia | 705/3 |
| 2012/0060216 A1* | 3/2012 | Chaudhri et al. | 726/21 |
| 2012/0078663 A1* | 3/2012 | Lorsch | 705/3 |
| 2012/0143626 A1* | 6/2012 | Jacobus et al. | 705/3 |
| 2012/0303896 A1* | 11/2012 | McGroddy-Goetz et al. | 711/118 |

OTHER PUBLICATIONS

Website Printout: "Inofile ChartMD will work with every ONC certified EMR."

(Continued)

*Primary Examiner* — Thu Nga Nguyen
(74) *Attorney, Agent, or Firm* — Finnegan, Henderson, Farabow, Garrett & Dunner, LLP

(57) ABSTRACT

A method for a data capturing and structuring includes determining at least one data capture mode for processing a non-electronic data record into an electronic data record and selecting a record owner having a plurality of existing data records to be associated with the electronic data record. The method also includes capturing the non-electronic data record into the electronic data record and collecting metadata from data associated with the record owner and the electronic data record and data generated during the capturing. Further, the method includes creating structured data records by combining the electronic data record and the metadata and exporting the structured data records.

9 Claims, 12 Drawing Sheets

(56) References Cited

OTHER PUBLICATIONS

Press Release, Fujitsu Computer Products of America, Oct. 24, 2011; "Fujitsu and Osmosyz Pioneer New Healthcare Standard for Electronic Clinical Documents; Interoperability Standard Identified by The Office of the National Coordinator for Health Information Technology", 3 pages.

PCT Notification International Search Report and Written Opinion in International Application No. PCT/US13/23846, International Filing Date: Jan. 30, 2013; Date of Mailing: Apr. 19, 2013.

* cited by examiner

DATA CAPTURING AND STRUCTURING METHOD AND SYSTEM

FIELD OF THE INVENTION

The present invention generally relates to data management technologies and, more particularly, to the methods and systems for data capturing and structuring.

BACKGROUND

The Internet and information technology make electronic data one of the most important aspects of running a business or even personal life. Data applications and systems are used in virtually all industries in many different ways. But the data generated by different applications and systems need to be managed, interpreted, and exchanged.

For example, healthcare organizations often utilize many different healthcare applications and systems to perform various services, both internal and external to the organizations. Much of the information collected by these applications and systems, such as data and documents, needs to be uploaded and shared among internal systems and external systems. However, the information collected often is unstructured.

Thus, a challenge currently faced by many healthcare organizations, despite their size, is that a large amount of unstructured contents generated on a daily basis are generally in native form and may be stagnant and unusable by the other applications. For example, unless a scanned document, a digital photo, or any electronic file, such as a PDF file, is uploaded and identified by a human, a healthcare application may be unable to identify what is in the file or who the file belongs to. Therefore, managing unstructured data in a healthcare organization is often expensive, time-consuming, and error-prone.

Another challenge faced by healthcare organizations is the difficulty to exchange unstructured files among healthcare organizations. As a result, oftentimes the files are printed and faxed to the recipients. This practice is not only time-consuming and expensive, but also leaves holes in the electronic patient record keeping, which may further cause security risks.

The disclosed methods and systems are directed to solve the problems set forth above and other problems.

BRIEF SUMMARY OF THE DISCLOSURE

One aspect of the present disclosure includes a method for data capturing and structuring. The method includes determining a data capture mode for processing a non-electronic data record into an electronic data record and selecting a record owner having a plurality of existing data records to be associated with the electronic data record. The method also includes capturing the non-electronic data record into the electronic data record and collecting metadata from data associated with the record owner and the electronic data record, and data generated during the capturing. Further, the method includes creating structured data records by combining the electronic data record and the metadata, and exporting the structured data records.

Another aspect of the present disclosure includes a computer storage medium storing computer executable programs. When executed by a processor in a data capturing and structuring device, the programs perform a data management method. The method includes determining a data capture mode for processing a non-electronic data record into an electronic data record and selecting a record owner having a plurality of existing data records to be associated with the electronic data record. The method also includes capturing the non-electronic data record into the electronic data record and collecting metadata from data associated with the record owner and the electronic data record, and data generated during the capturing. Further, the method includes creating structured data records by combining the electronic data record and the metadata and exporting the structured data records.

Other aspects of the present disclosure can be understood by those skilled in the art in light of the description, the claims, and the drawings of the present disclosure.

DETAILED DESCRIPTION

Reference will now be made in detail to exemplary embodiments of the invention, which are illustrated in the accompanying drawings.

Figure 1:
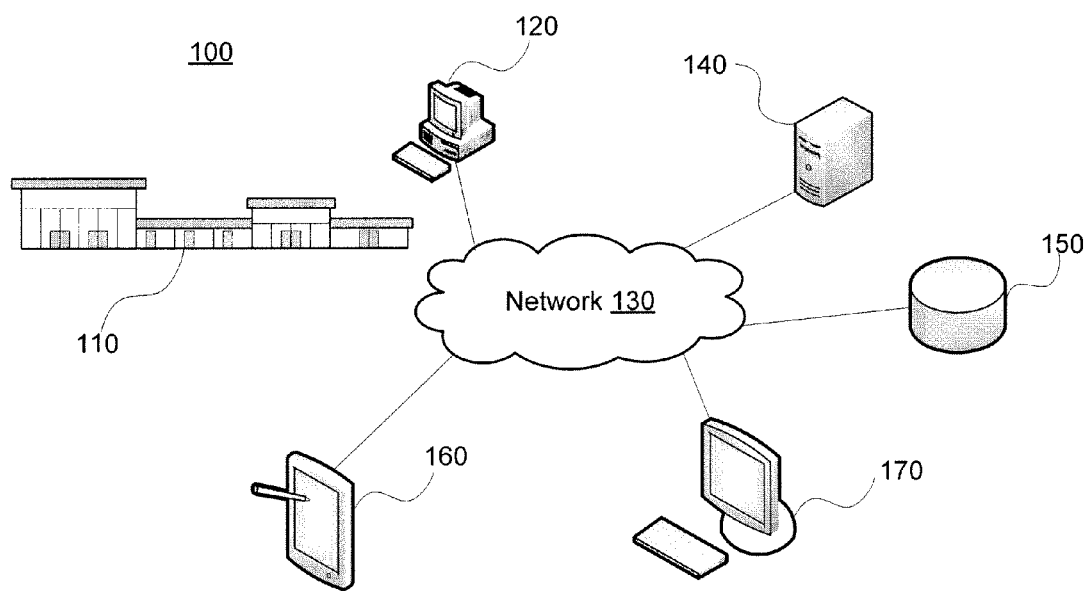
FIG. 1 illustrates an exemplary operating environment incorporating certain aspects of the disclosed embodiments.

FIG. 1 illustrates an exemplary operating environment incorporating certain aspects of the disclosed embodiments. As shown in FIG. 1, operating environment 100 may include a healthcare facility 110, a client workstation 120, a network 130, a server 140, a storage server 150, a healthcare user computer 160, and other user computer 170. Although singular entity is used for illustrative purposes, multiple facilities, workstations, and other devices may be used. Other components may be added and certain devices may be removed without departing from the principles of the disclosed embodiments.

Healthcare facility 110 may include any appropriate healthcare organization, such as a hospital, a laboratory, a medical center, or a clinic, etc. Healthcare facility 110 may have one or multiple client workstations 120 for performing certain data management functions.

A client workstation 120 may include any appropriate device with computing capabilities including certain multi-function devices. For example, a client workstation 120 may include a computer, a digital camera, a network scanner, a printer, a fax server, or any other multi-function device having computing functionalities, etc. Client workstation 120 may be an off-the-shelf multi-function device running particular software programs for performing disclosed data management processes or may be a customized multi-function device having disclosed data management functionalities.

Network 130 may include any appropriate type of network for exchanging data among various devices and computer systems. For example, network 130 may be a telecommunication network, a wireless network, or any private and public computer networks interconnected using certain standard protocols, such as the Internet.

Server 140 may include any appropriate computer servers, software, and databases so as to provide various enterprise and server-side services. For example, server 140 may run certain software programs to communicate and exchange data with client workstation 120 to complete various healthcare data management processes. Server 140 may also communicate with other external systems to exchange electronic medical records (EMR) or electronic healthcare records (EHD) based on certain data formats.

Storage server 150 may include one or more server computers configured to provide database services and database management services. Storage server 150 may be used to store any appropriate data in a central location or in a distributed storage system. Other systems may access data via the storage server 150.

Further, healthcare user computer 160 may include any appropriate computer system(s) used by healthcare professionals, e.g., doctors, nurses, and other healthcare providers or by healthcare organizations. Other user computer 170 may include any appropriate computer system(s) used by other non-healthcare professionals or organizations. Healthcare user computer 160 and/or other user computer 170 may receive data provided by client workstation 120 and/or server 140.

Figure 2:
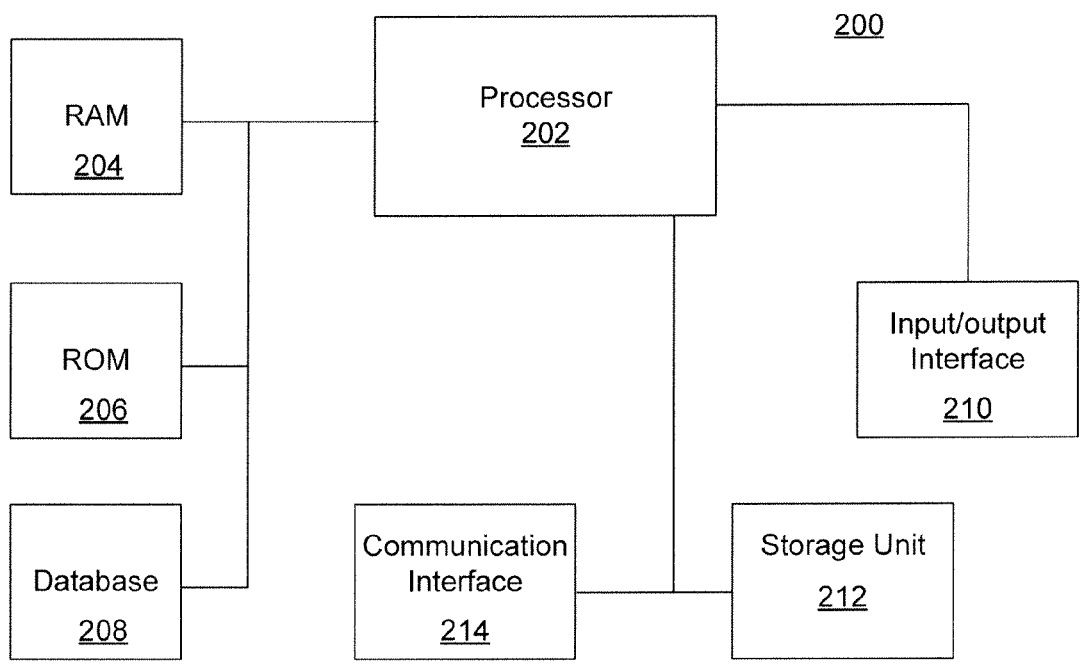
FIG. 2 illustrates a block diagram of an exemplary computing system consistent with the disclosed embodiments.

The various devices and computers (e.g., client workstation 120, server 140, or healthcare user computer 160) may be implemented using any appropriate computing systems and other peripheral or external devices. FIG. 2 shows a block diagram of an exemplary computing system 200.

As shown in FIG. 2, computing system 200 may include a processor 202, a random access memory (RAM) unit 204, a read-only memory (ROM) unit 206, a database 208, an input/output interface unit 210, a storage unit 212, and a communication interface 214. Other components may be added and certain devices may be removed without departing from the principles of the disclosed embodiments.

Processor 202 may include any appropriate type of graphic processing unit (GPU), general-purpose microprocessor, digital signal processor (DSP) or microcontroller, and application specific integrated circuit (ASIC), etc. Processor 202 may execute sequences of computer program instructions to perform various processes associated with computing system 200. The computer program instructions may be loaded into RAM 204 for execution by processor 202 from read-only memory 206.

Database 208 may include any appropriate commercial or customized database for computing system 200, and may also include query tools and other management software for managing database 208. Further, input/output interface 210 may be provided for a user or users to input information into computing system 200 or for the user or users to receive information from computing system 200. For example, input/output interface 210 may include any appropriate input device, such as a remote control, a keyboard, a mouse, a microphone, a video camera or web-cam, an electronic tablet, voice communication devices, or any other optical or wireless input devices. Input/output interface 210 may include any appropriate output device, such as a display, a speaker, or any other output devices. Further, input/output interface 210 may include any external device, such as a scanner, a camera, a fax, or a printer, etc.

Storage unit 212 may include any appropriate storage device to store information used by computing system 200, such as a hard disk, a flash disk, an optical disk, a CR-ROM drive, a DVD or other type of mass storage media, or a network storage. Further, communication interface 214 may provide communication connections such that computing system 200 may be accessed remotely and/or communicate with other systems through computer networks or other communication networks via various communication protocols, such as TCP/IP, hyper text transfer protocol (HTTP), etc.

Returning to FIG. 1, within healthcare facility 110 or within environment 100, various systems and/or various applications running on these systems may exchange information through network 130. More particularly, information such as metadata (i.e., data that describes or defines other data) may be exchanged over a specific messaging network (e.g., part of network 130) such that applications and systems can interactively process various types of data based on information exchanged over the messaging network. The physical medium for the messaging network may include any appropriate medium type, such as wireless network, cellular network, local LAN, or other wired or wireless network.

In certain embodiments, a messaging network based on health level seven (HL7) standard may be included in healthcare facility 110, and client workstation 120 and server 140 can listen or monitor the messaging network to obtain and update metadata for data capturing and structuring.

During operation, client workstation 120 may provide certain electronic healthcare record management processes to facilitate the healthcare data interoperability among different systems. As used herein, electronic healthcare records or electronic medical records may refer to any appropriate data, in electronic form, about a person's medical and healthcare status, activities, and history, etc. For example, the electronic medical records may include medical history (e.g., surgical history, medications, family history, social history, habits, immunization history, and development history), medical encounters (e.g., illness and treatment, physical examination, assessment and plan), orders and prescriptions, progress notes, test results, and other attached files and documents, such as digital images, consent forms, EKG tracings, and admission forms.

Figure 3:
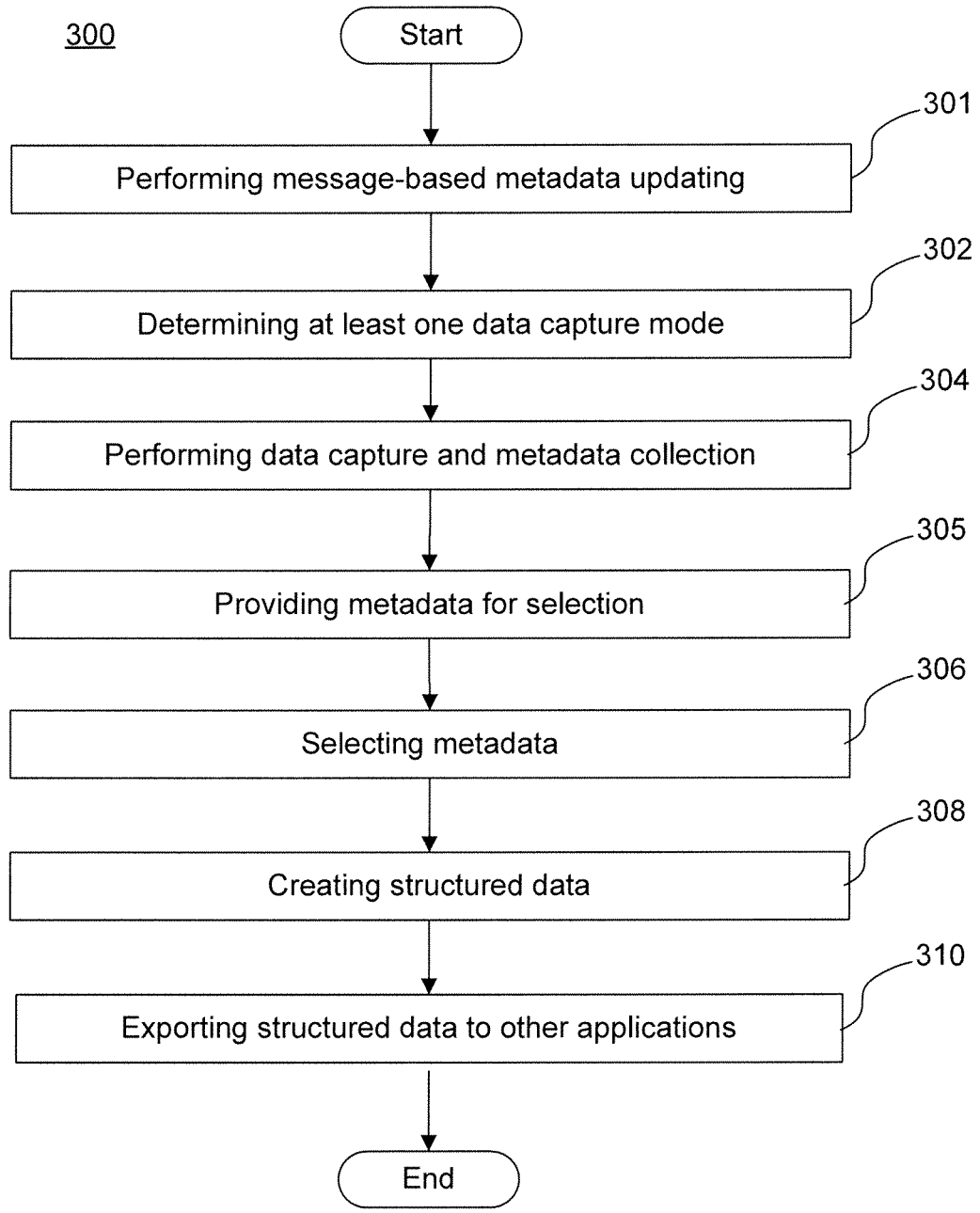
FIG. 3 illustrates an exemplary operating process consistent with the disclosed embodiments.

The electronic medical records may be provided by a healthcare provider in healthcare facility 110. For example, the healthcare provider may scan various medical records into electronic form. Then, to convert the scanned files from unstructured data to structured data, the healthcare provider may use client workstation 120 to perform collecting and packaging unstructured files or documents (e.g., scanned files in WORD, PDF, JPG, GIF, and TIFF, etc., formats) to make medical records electronically usable by information systems and applications in and out of healthcare facility 110. FIG. 3 illustrates an exemplary operating process 300 performed by client workstation 120 or, more particularly, by processor 202 of computing system 200 implementing client workstation 120.

As shown in FIG. 3, at the beginning of the operating process, processor 202 (e.g., client workstation 120, server 140) may perform message-based metadata updating (301). That is, processor 202 may automatically collect metadata based on communications on the messaging network. In other words, processor 202 may monitor HL7 messages and extract relevant data elements from received messages to be used as metadata.

The HL7 messages, as used herein, may refer to any appropriate messages used in HL7 messaging, which are used for communication and data integration between applications and systems within a healthcare facility or facilities. Table 1 illustrates exemplary HL7 messages used for obtaining metadata by processor 202.

TABLE 1

USING HL7 MESSAGES AND METADATA

| Message Type | Message Event | Description |
| --- | --- | --- |
| NEW ADMISSION/VISIT ADT—Admission/ Discharge/Transfer SIU—Schedule | A01 - New Admit A04 - New Registration A05 - Pre Admit | Indicates that a patient has been admitted or registered |
| DISCHARGE/CANCEL an ADMISSION/VISIT ADT—Admission/ Discharge/Transfer SIU—Schedule | A03 - Discharge A11 - Cancel Admit A13 - Cancel a discharge | Indicates that a patient has left the hospital or clinic or the appointment has been cancelled |
| PATIENT LOCATION ADT—Admission/ Discharge/Transfer | A02 - Transfer A12 - Cancel Transfer A17 - Bed Swap | Indicates that a patient has been transferred (or cancel a transfer) to another room or location |
| UPDATE PATIENT DETAIL ADT—Admission/ Discharge/Transfer | A08 - Update pt. info A31 - Update person info A18 - merge Pt. records A35 - change pt. Account number A36 - Change MRN | Update the patient record information (metadata) |
| ORMs Orders OBX ORU—Results | New Order Canceled Order Deleted Order Recurring Order Completed Order | Update the order information for a patient record |

As shown in Table 1, certain metadata, such as information about new admission/visit, discharge/cancel an admission/visit, patient location, update patient detail, ORMs orders and other results, may be automatically obtained from HL7 messaging and may used as metadata for data capturing and structuring.

Processor 202 may perform metadata updating continuously and interactively. For example, processor 202 of server 140 may receive messages from other systems over the messaging network and store the metadata received and may also forward the metadata to processor 202 of client workstation 120 for facilitating data capturing; while processor 202 of client workstation 120 may collect certain metadata and forward the metadata to processor 202 of server 140.

Further, processor 202 may determine at least one data capture mode (302). The term "data capture mode," as used herein, refers to a particular and systematic way to obtain an electronic medical record from a non-electronic medical record (e.g., a paper record) and to associate the obtained electronic medical record with a particular person or patient (i.e., a record owner). During operation, processor 202 may determine a data capture mode automatically based on pre-configured parameters or based on one or more inputs from a user (e.g., a nurse, a receptionist, a doctor, and so on).

More specifically, processor 202 may determine suitable data capture modes from a plurality of predetermined data capture modes. In certain embodiments, the plurality of predetermined data capture modes may include a "proximity-based capture" mode, an "event-based capture" mode, a "schedule-based capture" mode, an "inquiry-based capture" mode, and a "transaction-based capture" mode. Other data capture modes may also be used.

In the proximity-based capture mode, the distance between patients and client workstation 120 (e.g., a network scanner) is used to facilitate data capture. For example, the user can walk up to client workstation 120, log in, and see all the patients in that area. In other words, after authenticating the user, client workstation 120 may search all patients within a predetermined distance from the client workstation 120 to determine a list of patients fitting the proximity criteria and to further determine a particular patient for the electronic medical data. The distance may be entered by the user and the particular patient may also be selected by the user.

In the event-based capture mode, events happening in a certain time period are used to facilitate data capture. For example, the user can walk up to client workstation 120, log in, and see the events that have happened within a recent period of time and the patients associated with the events. In other words, after authenticating the user, client workstation 120 may search all patients associated with certain type(s) of event(s) within a predetermined time period to determine a list of patients fitting the event criteria and to further determine a particular patient for the electronic medical data. The time period may be inputted by the user and the particular patient may also be selected by the user.

In the schedule-based capture mode, a patient's schedule for upcoming and/or active visits is used to facilitate data capture. For example, the user can walk up to client workstation 120, log in, and see all the patients scheduled for a date entered. In other words, after authenticating the user, client workstation 120 may search all patients associated a particular schedule to determine a list of patients and to further determine a particular patient for the electronic medical data. The schedule (e.g., a date, a time period, etc.) may be inputted by the user and the particular patient may also be selected by the user.

Further, in the inquiry-based capture mode, certain search criteria entered by the user are used to facilitate data capture. For example, the user can walk up to client workstation 120, log in, and see all the patients matching the search criteria. In other words, after authenticating the user, client workstation 120 may search all patients based on the search criteria to determine a list of patients fitting the search criteria and to further determine a particular patient for the electronic medical data. The search criteria may be entered by the user. For instance, the user may enter a last name as search criteria to determine a patient with a matching last name. The particular patient may also be selected by the user.

In the transaction-based capture mode, a particular transaction(s) associated with existing medical records is used to facilitate data capture. For example, the user can walk up to client workstation 120, log in, and see the patient(s) having the existing medical record(s) associated with the particular transaction(s). In other words, after authenticating the user, client workstation 120 may search the patient(s) having medical records associated with the particular transaction(s) to determine a particular patient for the electronic medical data. Further, the transaction may be entered by the user. For instance, the user may enter original laboratory order information to determine the particular patient to associate a captured laboratory result.

Alternatively, client workstation 120 may search medical records of a particular patient to associate a particular transaction to the electronic medical record, and the particular patient may be determined by any other data capture mode. That is, client workstation 120 may first determine the patient based on other data capture mode or other information and then determine the particular transaction. For example, the user may select a patient based on the patient's last name and may then select the correct transaction to associate the data to be captured.

Further, these data capture modes may be used independently or in any appropriate combination. For example, one data capture mode may be used to reduce searching scope for another data capture mode to complete the data capture. After the data capture mode is determined, the particular patient(s) and/or particular medical record(s) may be determined to be associated with captured data.

In addition, these various data capture modes may be enabled and/or determined using the metadata from message-based metadata updating. For example, the metadata collected may be made available during the data capture process based upon the proximity, based upon an event, or based upon an inquiry by the user. That is, such metadata may be used to enable proximity-based, event-based, or inquiry-based capture mode and association to the correct set of metadata.

For example, patient location information (PATIENT LOCATION shown in Table 1) may be used for proximity-based data capture. Because the patient location data is already updated, client workstation 120 may automatically search the list of patient within the proximity using the most-updated information and without user's intervening. Further, admission/visit information (NEW ADMISSION/VISIT) may be used for event-based data capture. Because the new admission information is already forwarded to client workstation via the messaging network, an event can be used in real-time for identifying a particular record owner. Similarly, order information (ORMs) may be used for transaction-based data capture; and patient detail information (UPDATE PATIENT DETAIL) may be used to update patient information and may be used for inquiry-based data capture, and so on.

Returning to FIG. 3, after processor 202 determines the data capture mode (302), processor 302 may perform data capture and metadata collection (304). Processor 302 may perform data capture according to the data capture mode determined previously.

For example, in the proximity-based capture mode, a user (e.g., a nurse) working on the third floor of a hospital can log into client workstation 120 located on the third floor and see all the patients within the proximity of the client workstation 120 on the screen of client workstation 120. The user then selects the particular patient and scans a handwritten document to be associated with the patient.

Figure 4A:
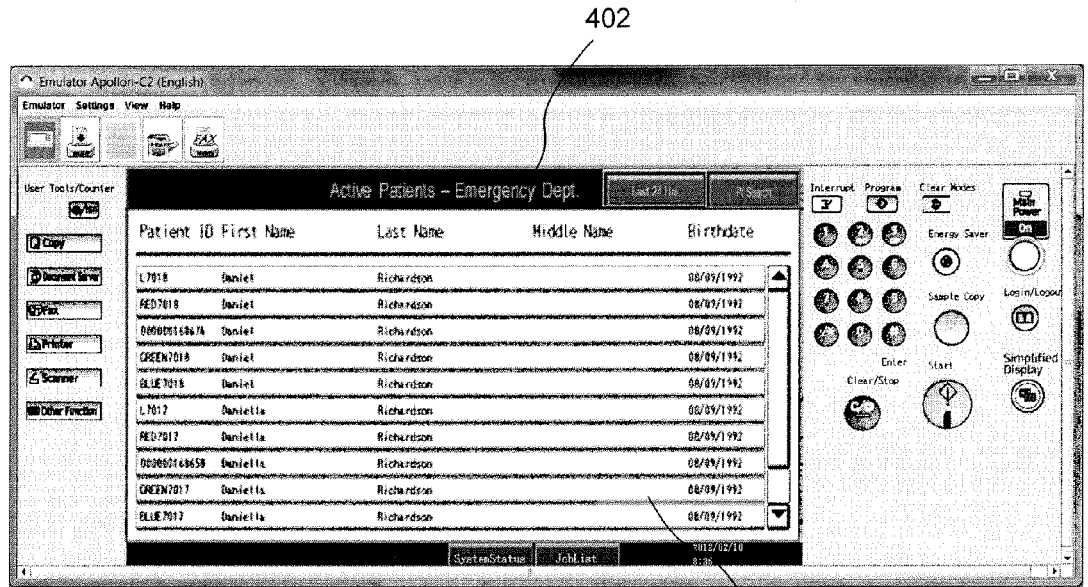
FIG. 4A-4B illustrate exemplary screen shots during a data capturing and structuring process consistent with the disclosed embodiments.
Figure 4B:
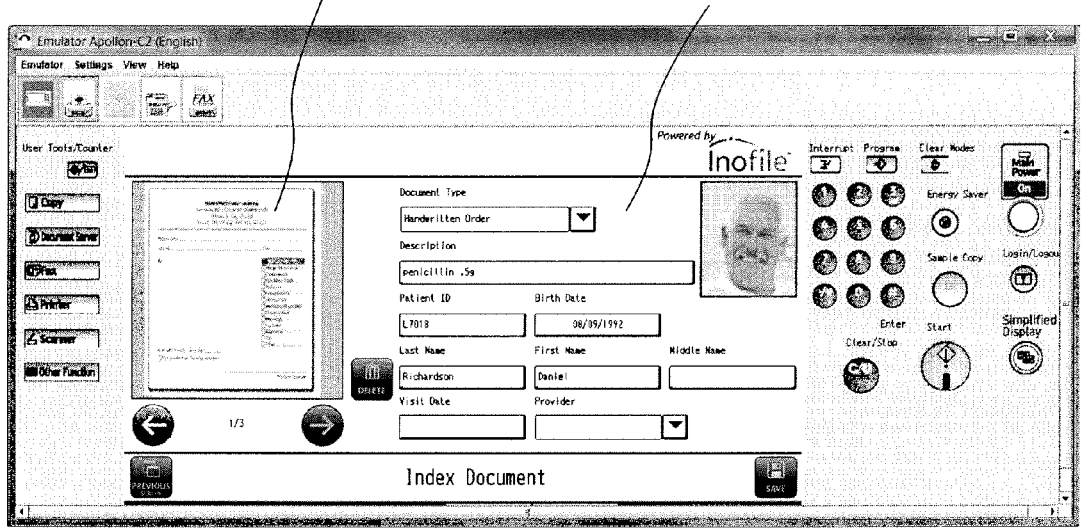

That is, after client workstation 120 searches and lists all patients within its proximity, client workstation 120 further receives an input from the user to determine a particular patient and obtains medical records and other information of the particular patient from a database or storage location. Further, client workstation 120 may cause the handwritten document scanned into an image or a file. Client workstation 120 may receive the scanned file and organize the file into the electronic medical records of the patient. FIGS. 4A-4B illustrate exemplary screen shots during this process.

As shown in FIG. 4A, a display bar 402 indicates that the proximity chosen is within the emergency department, and a patient list 404 is displayed by processor 202. Further, as shown in FIG. 4B, a scanned document 406 is displayed along with patient information 408 for a selected patient.

In the event-based capture mode, a user (e.g., a registration clerk) working at a hospital can register a patient, have the patient sign a consent form, walk up to client workstation 120, log in, and see the patients registered in the hospital in the last five minutes (i.e., the event). The user then selects the patient just registered and scans the consent form to be associated with the patient.

Figure 5A:
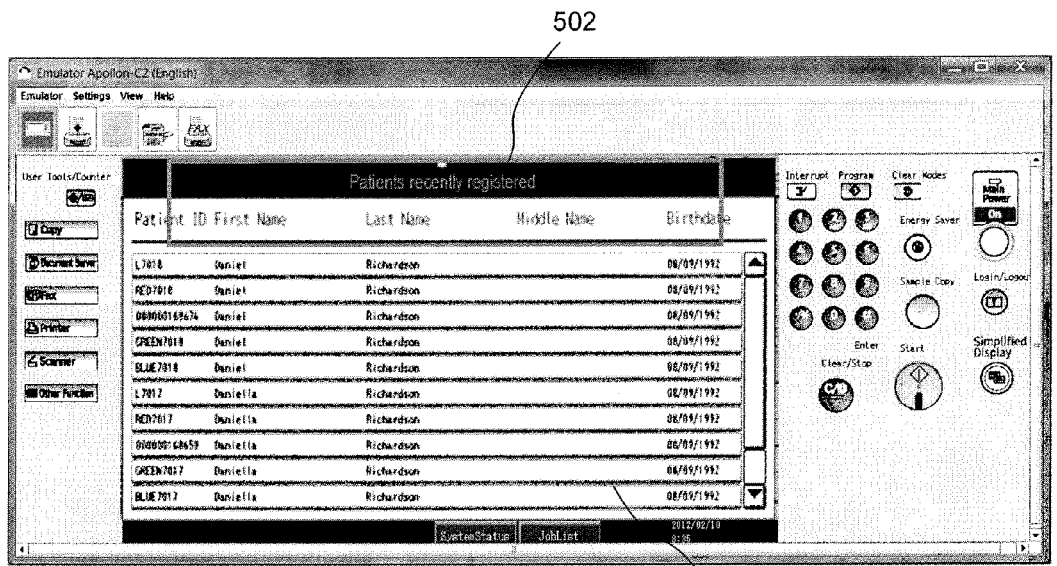
FIG. 5A-5B illustrate other exemplary screen shots during the data capturing and structuring process consistent with the disclosed embodiments.
Figure 5B:
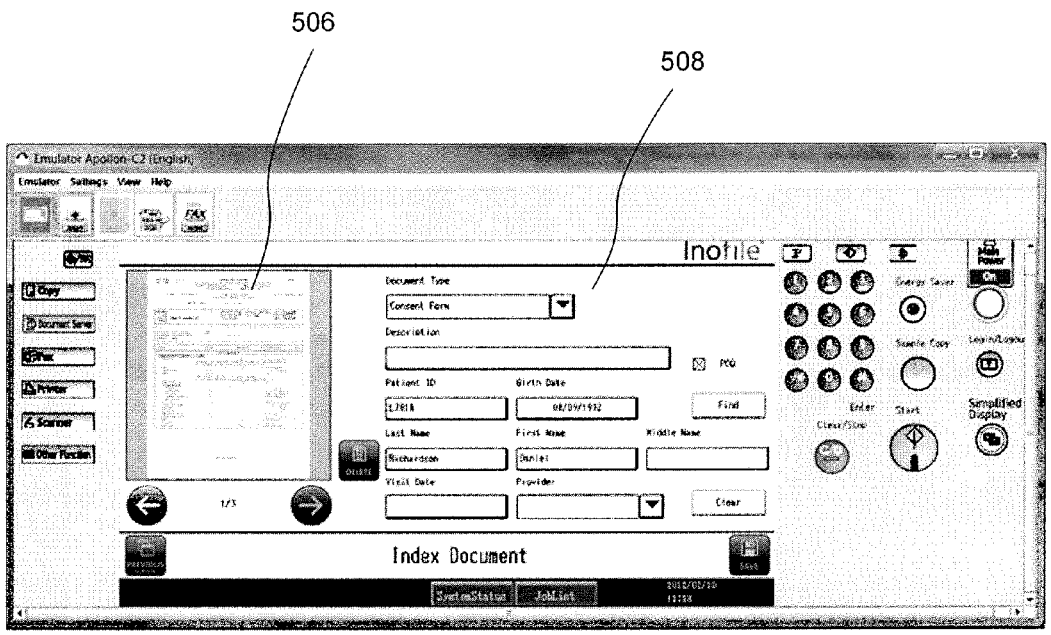

That is, after client workstation 120 lists all patients registered in the last five minutes, client workstation 120 further receives an input from the user to determine a particular patient and obtains medical records of the particular patient from a database or storage location. Further, client workstation 120 may cause the consent form scanned into an image or a file. Client workstation 120 may receive the scanned consent form and organize the file into the electronic medical records of the patient. FIGS. 5A-5B illustrate exemplary screen shots during this process.

As shown in FIG. 5A, a display bar 502 indicates that the event chosen is patients being recently registered, and a patient list 504 is displayed by processor 202. Further, as shown in FIG. 5B, a scanned consent form 506 is displayed along with the patient information 508.

In the schedule-based capture mode, a user working on managing the medical records and scanning historical files can walk up to client workstation 120, log in, enter the date for which the patient was scheduled as indicated in the historical files, and select the patient whose historical files are to be scanned. The user then scans historical files such as a patient chart.

Figure 6A:
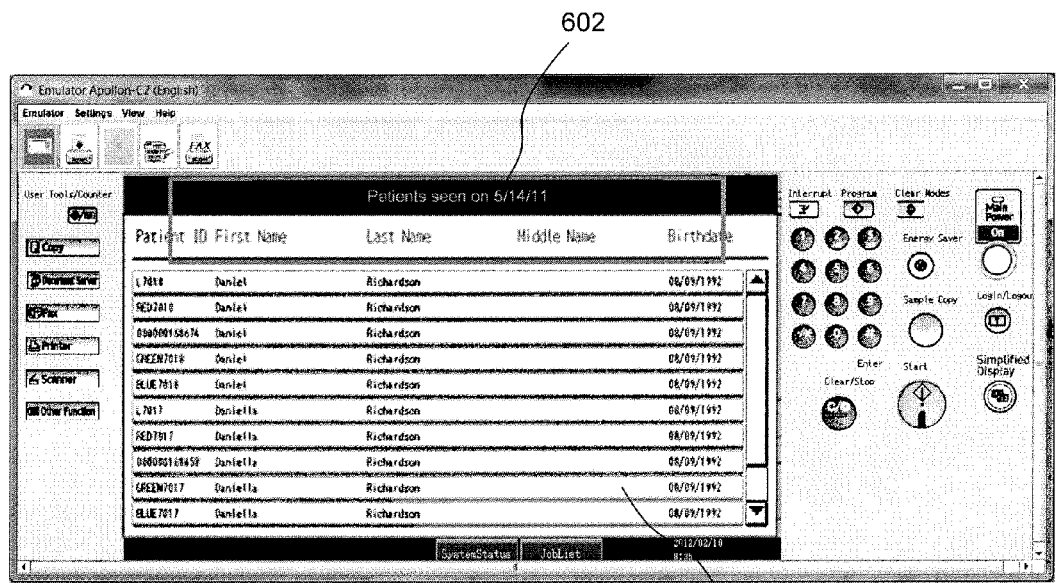
FIG. 6A-6B illustrate other exemplary screen shots during the data capturing and structuring process consistent with the disclosed embodiments.
Figure 6B:
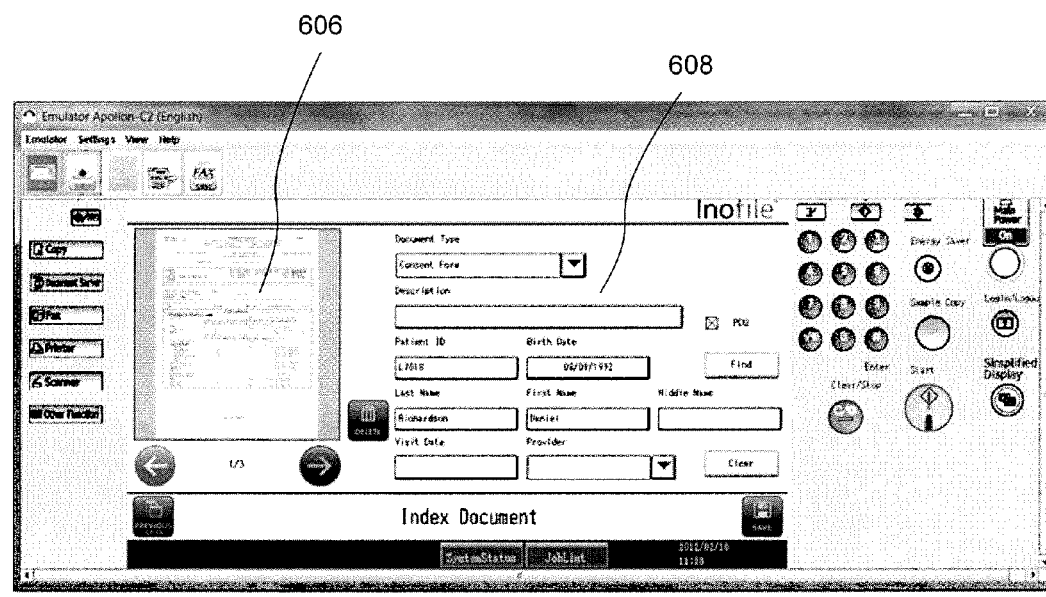

That is, after client workstation 120 lists all patients having the same schedule, client workstation 120 further receives an input from the user to determine a particular patient and obtains medical records of the particular patient from a database or storage location. Further, client workstation 120 may cause the historical document(s) scanned into an image(s) or a file(s). Client workstation 120 may receive the scanned document(s) and organize the file(s) into the electronic medical records of the patient. FIGS. 6A-6B illustrate exemplary screen shots during this process.

As shown in FIG. 6A, a display bar 602 indicating that the schedule chosen is for patients seen on May 14, 2011, and a patient list 604 is displayed by processor 202. Further, as shown in FIG. 6B, a scanned historical document 606 matching the schedule is displayed along with the patient information 608.

Further, in the inquiry-based capture mode, a user (e.g., a receptionist) can receive a file from a patient just walked in, walk up to client workstation 120, log in, key in the patient's last name, hit a search button, and find all patients matching the searched last name (i.e., the search criteria). The user then selects a correct patient and scans the file for the patient.

Figure 7A:
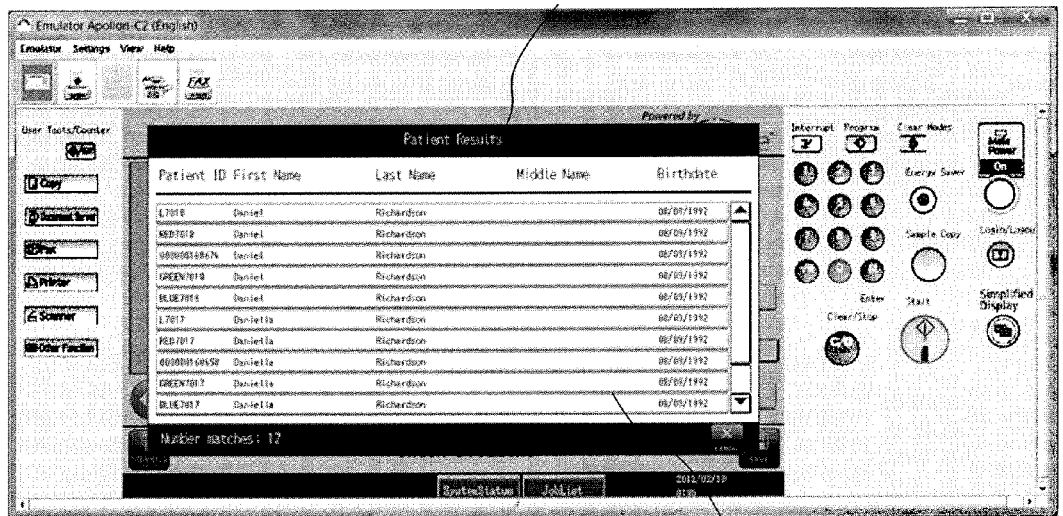
FIG. 7A-7B illustrate other exemplary screen shots during the data capturing and structuring process consistent with the disclosed embodiments.
Figure 7B:
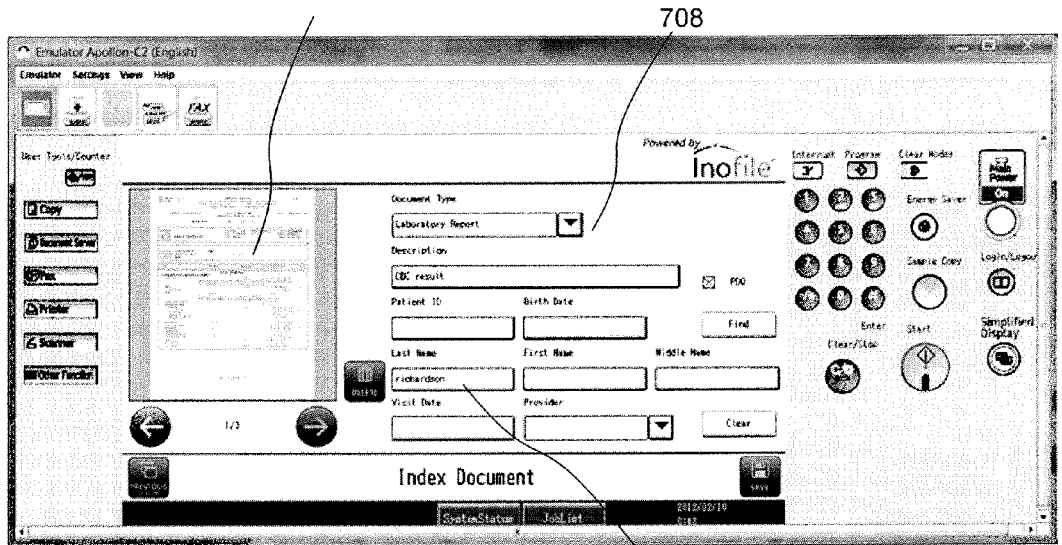

That is, after client workstation 120 lists all patients having the same last name, client workstation 120 further receives an input from the user to determine a particular patient and obtains medical records of the particular patient from a database or storage location. Further, client workstation 120 may cause the file scanned into an image(s) or a file(s). Client workstation 120 may receive the scanned document(s) and organize the file(s) into the electronic medical records of the patient. FIGS. 7A-7B illustrate exemplary screen shots during this process.

As shown in FIG. 7A, a display bar 702 indicates the search results, and a patient list 704 is displayed by processor 202. Further, as shown in FIG. 7B, a scanned document associated with the selected patient is displayed along with the patient information 708. Alternatively, the field of patient's last name 710 may be used to perform searching directly. That is, the user can enter the searched last name in field 710 to perform the search.

In the transaction-based capture mode, a user (e.g., a nurse) may receive a paper-based laboratory result which needs to be attached back to the original laboratory order that was already placed in the electronic medical records of a patient. The user selects the patient and visit, and the list of all orders placed for that visit are displayed on the screen on client workstation 120 (e.g., a network scanner). The user selects the correct order and scans the document to be associated with the correct order of the particular patient.

Figure 8:
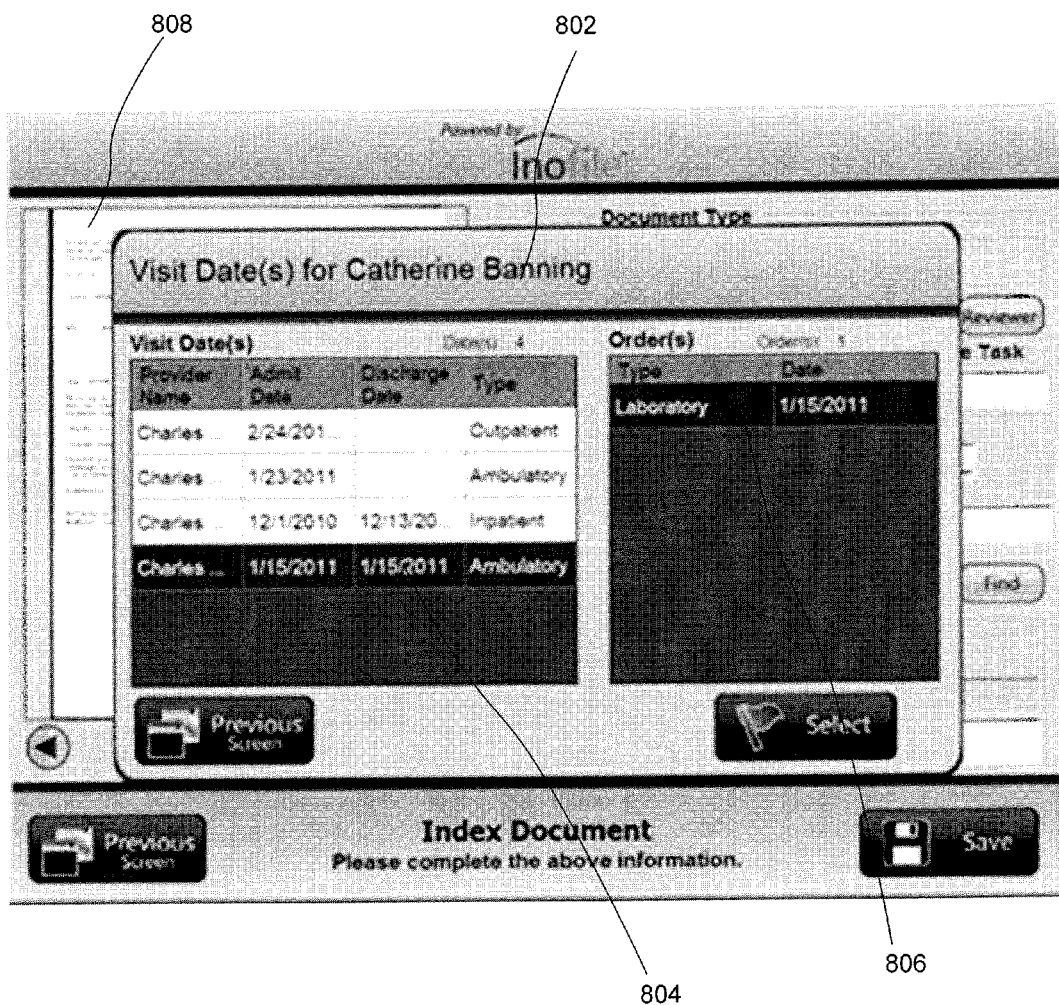
FIG. 8 illustrates another exemplary screen shot during the data capturing and structuring process consistent with the disclosed embodiments.

That is, client workstation 120 may first list all patients potentially associated with the laboratory result, e.g., having the same last name, etc. Client workstation 120 then receives an input from the user to determine a particular patient and obtains medical records of the particular patient from a database or storage location. Further, client workstation 120 may list all visits/orders of the patient and may receive input from the user to determine a particular visit and/or order to be associated with the laboratory result. Afterwards, client workstation 120 may cause the laboratory result scanned into an image(s) or a file(s). Client workstation 120 may receive the scanned document(s) and organize the file(s) into the electronic medical records of the patient. FIG. 8 illustrates an exemplary screen shot during this process.

As shown in FIG. 8, after the user selects a particular patient, a sub-window 802 is displayed with a title indicating the patient's visit dates. More particularly, the patient's name, admission date, discharge date, and type of visit, etc., are displayed in the sub-window 802. Further, an order is selected in the selection section 806 by the user as the order to be associated with the laboratory result. Afterwards, a scanned document 808 associated with the selected order is displayed along with the patient information (blocked).

During the data capture, the captured data, such as scanned files, are generally unstructured data or files. Processor 202 may also structure the unstructured data or files to make the captured data or files electronically usable by other information systems and applications in a healthcare or other type of environment. In certain embodiments, non-electronic data (e.g., papers, structures, other materials) may have been captured by other systems and may be inputted or transferred to processor 202 by other application/systems or by the user. It may be unnecessary for processor 202 to capture the data into electronic form. Processor 202 may skip the data capture and use the metadata to structure the collected data or the inputted unstructured data.

Processor 202 may structure the collected data using any appropriate methods. For example, processor 202 may wrapping the unstructured files or documents with appropriate metadata to create structured files or documents in various standard formats, including health level seven (HL7) standard, cross enterprise document sharing (XDS), extensible markup language (XML), and clinical document architecture (CDA). Other standards may also be used.

Processor 202 may select and obtain any appropriate metadata to convert the unstructured files to various structured files. For example, Table 1 illustrates exemplary metadata may be selected by processor 202.

TABLE 2

METADATA CATEGORIES/FIELDS

| Metadata Fields | Description |
| --- | --- |
| PATIENT INFORMATION | |
| Community Identifier | Unique identifier for a patient within a community or health information exchange |
| Patient Identifier (MRN) | Unique identifier for patient within a facility |
| Patient last name | Last Name of patient |
| Patient first name | First name of patient |
| Patient middle name | Middle name of patient |
| Patient suffix | Suffix for patient |
| Patient DOB | DOB of patient |
| Patient SSN | SSN of patient, if available |
| Photo of patient | Digital photo of patient, if available |

TABLE 2-continued

METADATA CATEGORIES/FIELDS

| Metadata Fields | Description |
| --- | --- |
| ADMISSION/VISIT INFORMATION | |
| Encounter Number (visit number/admission) | Unique identifier for a particular visit or admission to a hospital for a patient |
| Account Number | Unique identifier for the financial account number assigned to a patient |
| Visit Date | Date of beginning of visit or admission |
| Diagnosis - | Up to 4 DX codes |
| DRG | Diagnosis code/procedure sets for the visit |
| Admitting provider ID/Name | Provider that admitted the patient to the hospital |
| Attending provider ID/Name | Provider that is attending to the patient at the hospital |
| Referring provider ID/Name | Provider that is referring the patient to the hospital |
| Consulting provider ID/Name | Provider that is consulting to the patient |
| Location | Location of where the patient is being seen |
| Room/Bed | Room/bed of where the patient is being seen |
| Discharge Date | Date the patient was discharged from admission or visit |
| ORDER INFORMATION | |
| Order Date | Date of the order place |
| Order status | Status of the order |
| Order type | Type of the order placed |
| Ordering provider | Provider who order the test |
| Order ID | ID of the order |
| DOCUMENT (FILE) INFORMATION | |
| Document Name | Name of the document |
| Document description | Description of the document |
| Document type | Type of the document |
| Document date | Date of the document |
| Document status | Status of the document (active, inactive, signed, unsigned, etc.) |
| Author | Who created the document |
| Authenticator | Who signed the document |
| Confidentiality Code | Confidentiality level of the document |
| Custodian | Who is the custodian of the document |
| Custodian address & telephone | Custodian address and telephone |
| Data Enterer | Who is the data enterer/scanner of the document |
| Language Code | What language is the document in |
| SYSTEM INFORMATION | |
| Originating source information | Where did the file come from |
| Originating source system information | Information about the system that generated the content |
| FILE INFORMATION | |
| Reference to external file or embedding of binary of file | Original unstructured file reference or embedding of the file within the structured file |

As shown in Table 2, data about relevant patient information, such as admission/visit information, order information, document (file) information, system information, and file information, etc., may be obtained by processor 202 and used as metadata to structure the unstructured files and documents. The metadata may include data obtained from the patient's existing records as well as dynamically obtained data associating with the captured data.

More specifically, processor 202 may obtain metadata during the data capture process. That is, during the same data capture process, processor 202 may obtain certain metadata required for structuring data in real-time. Further, certain metadata may be automatically obtained during the data capture, while certain other metadata may be entered by the user for structuring the captured files.

As explained previously, metadata can also obtained by receiving HL7 messages in the messaging network. Each HL7 message may contain multiple segments that have relevant metadata. Processor 202 may obtain the metadata based on the different segments. For example, the segments may include:

MSH—Header segment regarding message, date/time, and originating source

EVN—Identifying the event of the message

PID—Containing information about the patient

PV1, PV2—Containing the information about the patient visit/admission

DG1—Containing the diagnosis information

OBX—Containing information about the order information

Because HL7 messages can be obtained dynamically, the metadata obtained may be stored in a location for later data capture, used for current data capture, and/or used for updating existing metadata. For example, information about a new patient, visits and location information, orders, or patient updates may be used to update patient's medical records and to be fed back to any current and/or future proximity-based data capture, event-based data capture, and transaction-based data capture, etc. Other metadata and/or messages may also be used.

Returning to FIG. 3, after performing the data capture and metadata collection (304), processor 202 may provide the metadata for selection (305). For example, processor 202 may provide the available metadata on a display screen for the user to choose particular types of metadata, so-called pushing-to-screen method. Processor 202 may use other ways to provide the metadata for proper metadata selection.

Further, processor 202 may select desired metadata (306). Processor 202 may select metadata based on any appropriate information, such as the type and attributes of the unstructured data, the structured data format(s), the purpose and usage of the later structured data, etc. Processor 202 may also select metadata based on user's selection of particular types of metadata.

Further, processor 202 may select metadata from different sources at the same time. For example, processor 202 may select certain static metadata, the metadata that is not frequently changed or that is same for most patients. Processor 202 may also select certain dynamic metadata, such as data obtained during the data collection process or metadata updating, which may be different for different patients. Further, processor 202 may also select certain automatically detected metadata, such as data from real-time messaging or other communications. In addition, processor 202 may select different types of metadata at the same time according to different types of structured files or documents to be created.

After selecting the metadata (306), processor 202 may create the structured data (308). Processor 202 may create the structured data by attaching the metadata to the unstructured file. That is, processor 202 may combine and package the unstructured file or document with the selected metadata and, optionally, additional static metadata held within the setup of the data management system (e.g., client workstation 120, server 140, etc.).

Further, the file and data are then converted dynamically to a desired structured format or multiple desired structured formats based upon the document type, the configuration setup by the healthcare organization, or other workflow considerations. For example, processor 202 may convert the file and data to structured file formats such as XML, CDA, XDS, or an HL7 message. The formats may be determined based upon the document type and different systems within the healthcare facility, and/or may be configured in the settings of client workstation 120 and/or server 140. Optionally, processor 202 may create multiple structured files at the same time, and each structured file may have a different structure format. In this way, the file or document may only need to be scanned once and can be used by multiple applications and systems.

Figure 9:
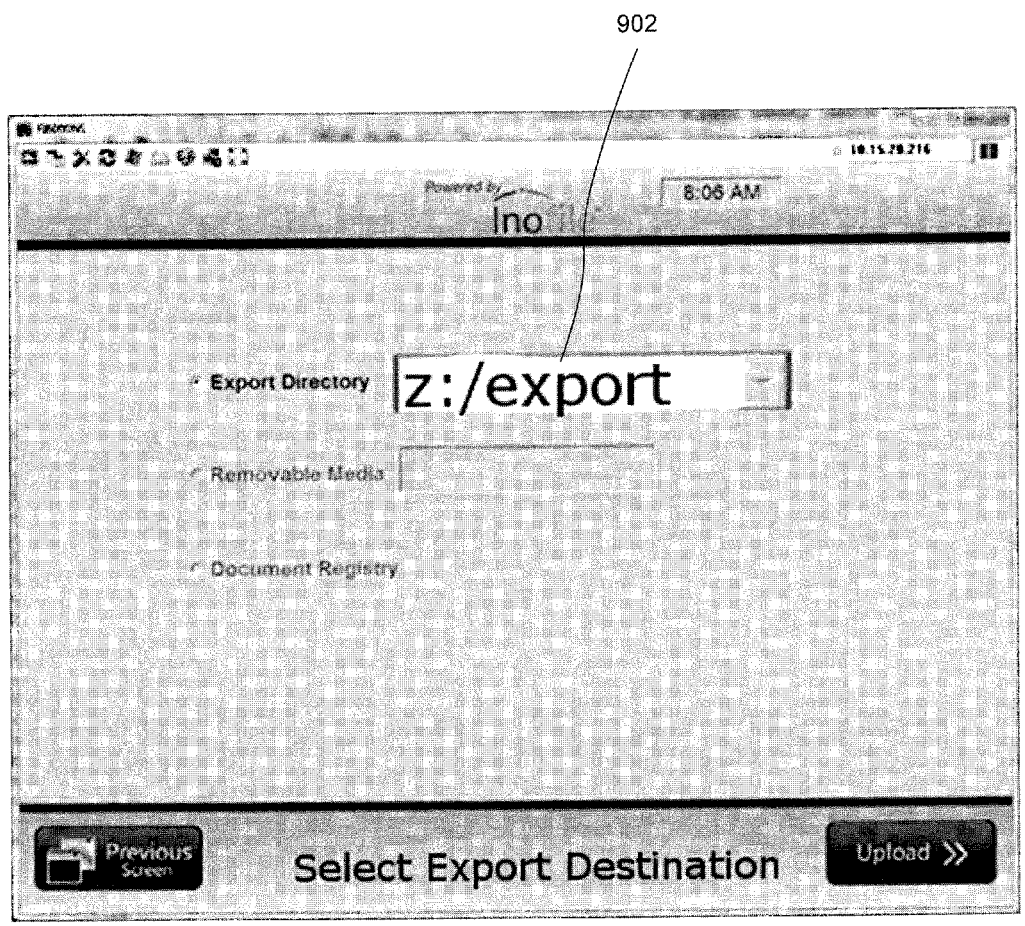
FIG. 9 illustrates another exemplary screen shot during the data capturing and structuring process consistent with the disclosed embodiments.

In addition, processor 202 may export the structured data to other applications (310). That is, newly formed structured contents may be submitted to other applications and systems. The receiving applications or systems may be internal in the healthcare facility or may be external systems or applications. Processor 202 may export the structured files automatically using a preconfigured list or based on a user input. Further, processor 202 may export the structured files based upon the preferences of the recipient. FIG. 9 illustrates an exemplary screen shot during this process.

As shown in FIG. 9, the user may configure or specify a particular destination for exporting the structured file. The screen interface allows the user to select an export destination or an export directory. The data field 902 indicating a location inputted by the user for exporting the structured file, which is set to "z:/export." The export destination may be a local directory, a network storage directory, or a network drive mapped to any appropriate application or system.

Thus, the data capturing and structuring process may be completed in a single process or in one pass. The structured files are generated dynamically and can be exported to any designated system(s) or application(s) using standardized transport protocols including XDS.b, XDR, XDM, and Direct messaging, etc.

The receiving applications or systems may automatically import the packaged contents (i.e., the structured file) and may include the contents in the proper medical records within the receiving applications or systems. Processor 202 may also receive structured files from other applications and systems and may also automatically import the packaged contents (i.e., the structured file) and may further associate the contents with the proper medical records within its own applications. Other processing may also be performed. For example, the metadata collected during the data capturing and structuring process is further forwarded to other applications and systems over the messaging network (i.e., network 130) for continued metadata updating such that an interactive metadata generation, application, and combination with unstructured data can be achieved.

Figure 10:
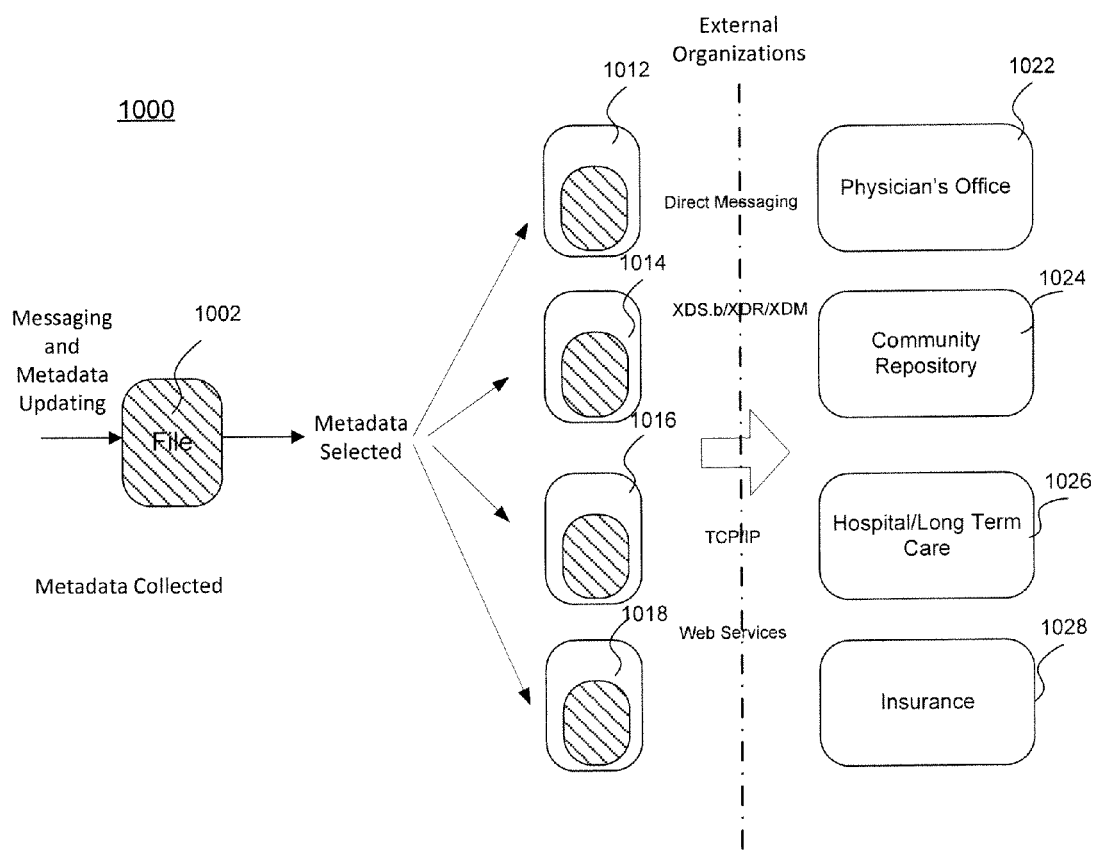
FIG. 10 illustrates an exemplary data structuring and exporting process consistent with the disclosed embodiments.

FIG. 10 illustrates an exemplary data structuring and exporting process 1000 with respect to an unstructured file 1002. As shown in FIG. 10, the metadata is updated by messaging to enable various data capture modes, and an unstructured file 1002 is created with one or more data capture modes during the data capture process as previously described and various metadata is also collected by the message updating and during the data capturing process. Also, during and/or at end of the data capture process, metadata is selected to be combined with or wrapped around the unstructured file 1002 to create a plurality of structured files. The metadata and/or structured files can also be sent over the messaging network to update other applications and systems.

For example, the file may be converted to a CDA file 1012, an XDS file 1014, an XML file 1018, and/or an HL7 message 1016, etc. The formats may be determined based upon the document types and systems within the healthcare facility. The formats may also be configured within the settings of the application for data structuring.

After a file has been packaged in a structured format, the file can be converted and sent on demand or through pre-configured rules to internal systems and/or external systems. For example, the CDA file 1012 may be sent to a physician's office; the XDS file 1014 may be sent to a community repository; the HL7 message/file 1016 may be sent to a hospital or long term care provider; and the XML file 1018 may be sent to an insurance company. These examples are used for illustrative purposes and any appropriate recipients may be used. Further, these files may be sent using different communication protocols. For example, these files may be sent over direct messaging, XDS.b/XDR/XDM protocols, TCP/IP protocols, and web services, etc. Other protocol may also be used.

Further, the above mentioned process 1000 may be integrated into a healthcare service workflow. For example, a receptionist at a physician office receives a call from a referring physician for a patient to have a specific report sent over for a patient being seen by the physician. The receptionist finds the report, searches and assigns to the correct patient, scans the document, and then selects the location for submission based upon the screen displayed. The file is packaged and sent over using the standardized protocol for submission.

Figure 11:
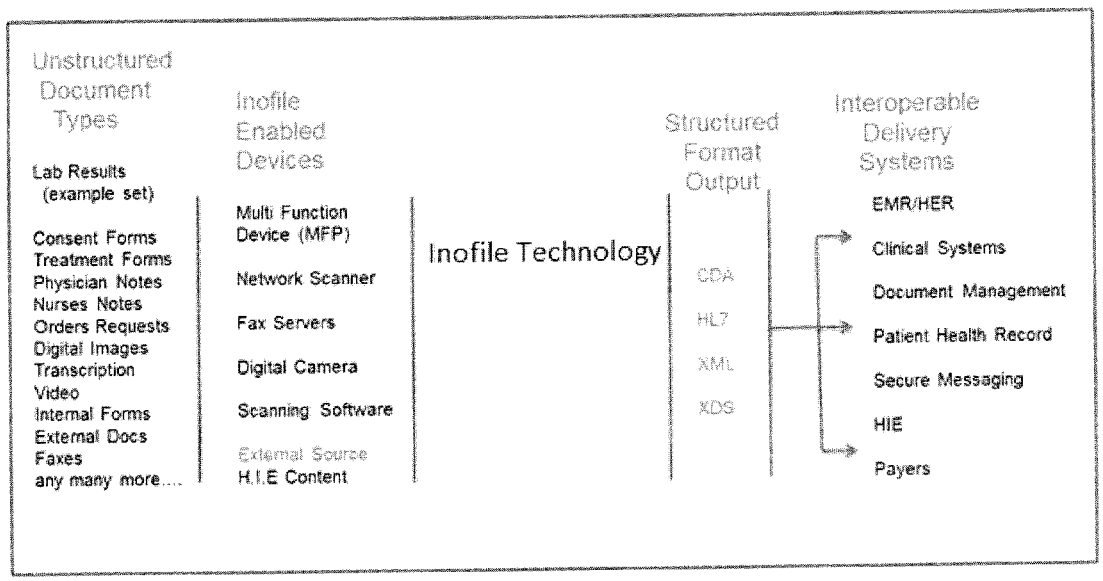
FIG. 11 illustrates various exemplary elements for data capture and structuring consistent with the disclosed embodiments.

In addition, the disclosed methods and systems may involve various document types and other features. FIG. 11 illustrates various exemplary unstructured document types, client workstation types, structured data formats, and recipient system types. Relationships among these various types may be created to determine the data capturing and structuring processes.

Figure 12:
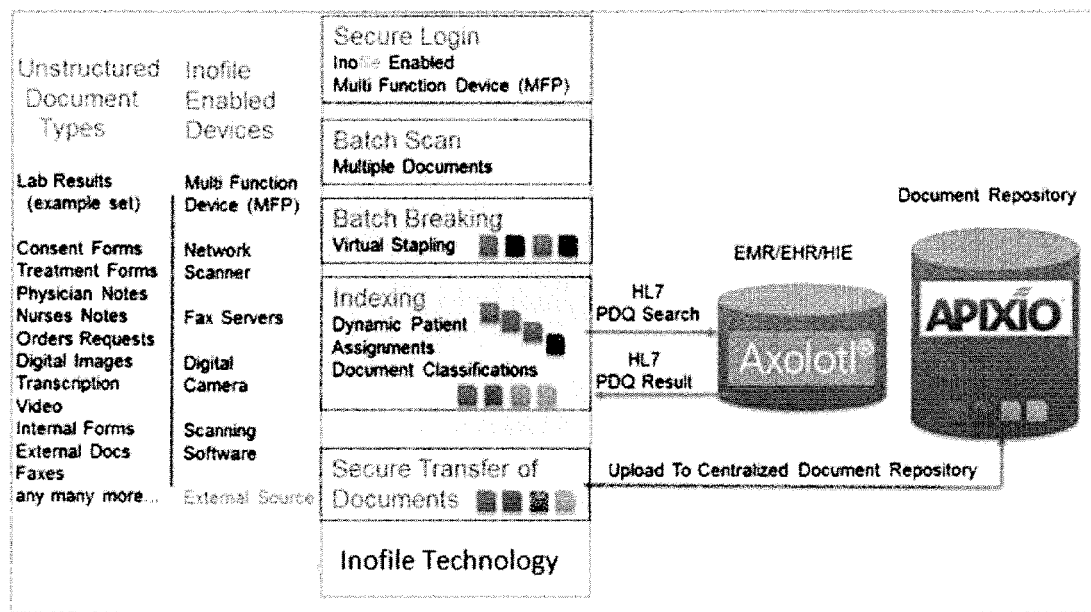
FIG. 12 illustrates various exemplary features for data capture and structuring consistent with the disclosed embodiments.

FIG. 12 illustrates various exemplary features for data capturing and structuring. For example, as shown in FIG. 12, a secure login feature may be provided in client workstation 120 (e.g., a multi-function device) for authenticating the users; a batch scanning feature may be provided to scan multiple documents after the particular patient is selected; a batch breaking feature may be provide for separate electronic records into virtual files (e.g., virtual stapling); an indexing feature may be provided for dynamic patient assignments and document classifications; and a secure transfer of documents feature may be provided to send structured documents to various recipients. Further, server 140 and/or client workstation 120 may also exchange structured files with other systems, such as an EMR/EHR/HIE server or a document repository server.

The disclosed systems and methods may provide many advantageous healthcare data management applications. For example, because metadata for structuring data is collected during the same data capture process, and metadata selection is also performed during or at end of the data capture, the data structuring efficiency and accuracy can be substantially increased. Further, the data capturing process includes a variety of data capture modes to fit various circumstances. In addition, the automatically collected metadata may be used to enable data capture modes to further increase the flexibility and efficiency of the application. Multiple structured formats from a single unstructured file or document can be generated such that the multiple structured files can be submitted to and used by multiple systems in various healthcare settings through standardized transport protocols.

Although the disclosed systems and methods are illustrated in a healthcare environment, applications in other industries can also apply the disclosed systems and methods for data structuring and other data management functions. For example, in legal industry, real property industry, or other financial and business environments, a large amount unstructured legal documents can be efficiently structured by using the disclosed systems and methods. Other applications, improvements, and modifications are obvious to those skilled in the art.

What is claimed is:

1. A method for data capturing and structuring, comprising:
   receiving, by a processor in a data processing environment, input corresponding to an outstanding order;
   determining, by the processor and based the received input corresponding to the outstanding order, at least one record owner having an order corresponding to the received input;
   generating, using the processor, an order-based capture mode including at least one record owner having an outstanding order corresponding to the received input, the order-based capture mode for associating an unstructured document with a record owner;
   capturing, using the processor, the unstructured document under the order-based capture mode;
   determining, using the processor, the record owner from the at least one record owner having an outstanding order corresponding to the received input having at least one existing data record to be associated with the unstructured document by comparing the at least one existing data record with the captured unstructured document;
   collecting metadata from data associated with the record owner, the unstructured document, and data generated during the capturing;
   creating the structured document using the metadata;
   exporting the structured document; and
   importing the structured document by a receiving application.

2. The method according to claim 1, wherein:
   the existing data records are electronic medical records; and
   the record owner is a patient.

3. The method according to claim 1, further including:
   updating the metadata dynamically based on data received from a messaging network.

4. The method according to claim 1, wherein collecting metadata includes:
   collecting both static metadata and dynamic metadata.

5. The method according to claim 1, wherein creating structured documents further includes:
   creating the structured documents in one of a health level seven (HL7) format, a cross enterprise document sharing (XDS) format, an extensible markup language (XML) format, and a clinical document architecture (CDA) format.

6. The method according to claim 1, wherein creating structured documents further includes:
   creating multiple structured documents in two or more formats from a health level seven (HL7) format, a cross enterprise document sharing (XDS) format, an extensible markup language (XML) format, and a clinical document architecture (CDA) format.

7. The method according to claim 1, wherein:
   the metadata is collected from an HL7 message received by the processor.

8. The method according to claim 1, wherein exporting the structured documents further includes:
   exporting the structured documents to multiple recipients in multiple formats, wherein the metadata is selected based on the recipients and the multiple formats are generated based on the recipients.

9. A non-transitory computer storage medium storing computer executable programs for, when being executed by a processor in a data capturing and structuring device in a data processing environment, performing a data management method comprising:
   receiving, by a processor in a data processing environment, input corresponding to an outstanding order;
   determining, by the processor and based the received input corresponding to the outstanding order, at least one record owner having an order corresponding to the received input;
   generating, using the processor, an order-based capture mode including at least one record owner having an outstanding transaction corresponding to the received input, the order-based capture mode for associating an unstructured document with a record owner;
   capturing, using the processor, the unstructured document under the order-based capture mode;
   determining, using the processor, the record owner from the at least one record owner having an order corresponding to the received input having at least one existing data record to be associated with the unstructured document by comparing the at least one existing data record with the captured unstructured document;

collecting metadata from data associated with the record owner, the unstructured document, and data generated during the capturing;

creating the structured document using the metadata;

exporting the structured document; and importing the structured document by a receiving application.

* * * * *